(12) United States Patent
Li et al.

(10) Patent No.: US 9,796,136 B2
(45) Date of Patent: Oct. 24, 2017

(54) AUTOMATIC LABELLING MACHINE AND AUTOMATIC LABELLING MACHINE CONTROL METHOD

(71) Applicant: Shandong New Beiyang Information Technology Co., Ltd, Shandong (CN)

(72) Inventors: Hongyuan Li, Shandong (CN);
Xunpeng Wang, Shandong (CN);
Mingbo Chi, Shandong (CN)

(73) Assignee: Shandong New Beiyang Information Technology Co., Ltd., Beijing (CN)

( * ) Notice: Subject to any disclaimer, the term of this patent is extended or adjusted under 35 U.S.C. 154(b) by 0 days.

(21) Appl. No.: 15/037,614

(22) PCT Filed: Sep. 22, 2014

(86) PCT No.: PCT/CN2014/087119
§ 371 (c)(1),
(2) Date: May 18, 2016

(87) PCT Pub. No.: WO2015/078223
PCT Pub. Date: Jun. 4, 2015

(65) Prior Publication Data
US 2016/0288410 A1    Oct. 6, 2016

(30) Foreign Application Priority Data
Nov. 29, 2013   (CN) .......................... 2013 1 0629027

(51) Int. Cl.
*B65C 9/40*    (2006.01)
*B29C 65/78*    (2006.01)
(Continued)

(52) U.S. Cl.
CPC ................ *B29C 65/78* (2013.01); *B65C 3/14* (2013.01); *G01N 35/00732* (2013.01); *B29L 2009/00* (2013.01); *G01N 2035/00861* (2013.01)

(58) Field of Classification Search
CPC ....... B29C 65/78; B29L 2009/00; B65C 3/14; B65C 3/163; B65C 9/40; B65C 2009/404;
(Continued)

(56) References Cited

U.S. PATENT DOCUMENTS

2008/0271852 A1* 11/2008 Giacalone ................. B65C 3/16
156/361
2014/0125797 A1* 5/2014 Matsumoto ............ G06Q 50/22
348/129

FOREIGN PATENT DOCUMENTS

CN    101146715 A    3/2008
CN    101269711 A    9/2008
(Continued)

OTHER PUBLICATIONS

International Search Report mailed on Nov. 28, 2014, in the International Application No. PCT/CN2014/087119, filed Sep. 22, 2014, 6 pages.

*Primary Examiner* — George Koch
(74) *Attorney, Agent, or Firm* — Wilmer Cutler Pickering Hale and Dorr LLP

(57) ABSTRACT

Disclosed are an automatic labeling machine and an automatic labeling machine control method. The automatic labeling machine is used for adhering an identification label on a surface of a test tube. The automatic labeling machine comprises: a tube insertion port (80) used for inserting a test tube; a controller (4) used for determining the type of test tube to be inserted; and a prompting apparatus (3) connected to the controller (4) and used for outputting prompting information corresponding to the type of the test tube to be (Continued)

inserted. The problem of automatic labeling machines easily causing a test tube selection error in the prior art is solved.

8 Claims, 9 Drawing Sheets

(51) Int. Cl.
*B65C 3/14* (2006.01)
*G01N 35/00* (2006.01)
*B29L 9/00* (2006.01)

(58) Field of Classification Search
CPC ........ B65C 2009/405; B65C 2009/407; B65C 2009/408; G01N 35/00732; G01N 2035/00861
USPC .................... 156/64, 351, 378, 379, DIG. 44
See application file for complete search history.

(56) References Cited

FOREIGN PATENT DOCUMENTS

| | | |
|---|---|---|
| CN | 101811586 A | 8/2010 |
| CN | 202226111 U | 5/2012 |
| CN | 103612804 A | 3/2014 |
| JP | 2002255140 A | 9/2002 |
| JP | 2005067660 A | 3/2005 |
| WO | WO-2013/108169 A1 | 7/2013 |

* cited by examiner

AUTOMATIC LABELLING MACHINE AND AUTOMATIC LABELLING MACHINE CONTROL METHOD

REFERENCE TO RELATED APPLICATION

This Application is a National Stage Entry of PCT International Application No. PCT/CN2014/087119, filed Sep. 22,2014, which claims priority to CN Application 201310629027.2, filed Nov. 29, 2013, the contents of which are incorporated herein by reference in their entirety.

TECHNICAL FIELD

The present disclosure relates to the field of labeling machine, and in particular to an automatic labeling machine and an automatic labeling machine control method.

BACKGROUND

Blood-sumpling collection by using a vacuum test tube has becoming popular. Due to difference in items of blood test, different addictives such as separation gel or coagulant or the like are added into the vacuum test tube in advance. The test tubes are encapsulated with covers of different color depending on the type of the addictives added into the test tube so as to facilitate classification and management. For example, the test tube with a red cover is placed with general serum in advance, and the test tube with a green cover is placed with heparin anticoagulant in advance.

In order to mark the blood sample collected by institutions such as blood banks, hospitals or biochemical laboratories, an identification label needs to be adhered to the surface of the test tube. The identification label has been printed sample detection information, collector personal information or the like printed thereon. FIG. 1 is a structural schematic of an automatic labeling machine of the existing technology. As illustrated in FIG. 1, the automatic labeling machine includes a printing apparatus 1' and a labeling apparatus 2' positioned in a discharge port of the printing apparatus 1'. After collecting the blood sample, the operator determines the type of the vacuum test tube 5' and color of the cover thereof according to the item to be detected, and then inserts the vacuum test tube 5' with the corresponding color cover into the labeling apparatus 2' through a tube insertion port 4'. The printing apparatus 1' performs the printing task and outputs a label. The label output by the printing apparatus 1' is then adhered to the surface of the vacuum test tube 5' by the labeling apparatus 2'.

Due to multiple categories of the vacuum test tube, however, the type of the test tube has to be check and the corresponding type of test tube has to be selected manually when such automatic labeling machine is used for adhering label to the surface of the vacuum test tube. For instance, when check of the color of the cover of the test tube and selection of the test tube with the cover of the corresponding color are done manually, mistake may likely be made during this process, which lead to a problem of a wrong detection result.

SUMMARY

A main object of the present disclosure is to provide an automatic labeling machine and a control method therefor so as to address the problem of selection error of the test tube suffered from the automatic labeling machine of the existing technology.

To achieve the above object, according to one aspect of the present disclosure, an automatic labeling machine for adhering an identification label to the surface of a test tube is provided. The automatic labeling machine may include: a tube insertion port for inserting the test tube; a controller for determining the type of the test tube to be inserted; and a prompting apparatus connected to the controller and used for outputting a prompting information corresponding to the type of the test tube to be inserted.

Further, the controller is used for determining a color of a cover of the test tube to be inserted, and the prompting apparatus is used for outputting the prompting information corresponding to the color of the cover of the test tube to be inserted.

Further, the automatic labeling machine may further include a storage apparatus that is used for storing a correspondence relation between the type of the test tube and the color of the cover of the test tube, where the controller is connected to the storage apparatus, so as to receive printed data, determine the type of the test tube to be inserted according to the printed data, and then search for the correspondence relation between the type of the test tube and the color of the cover of the test tube stored in the storage apparatus and determine the color of the cover of the test tube to be inserted according to the type of the test tube to be inserted.

Further, the prompting apparatus may include any one of the following prompting apparatuses or any combination thereof: a color prompting apparatus used for outputting a color which corresponds to the color of the cover of the test tube to be inserted that is determined by the controller; a voice prompting apparatus used for outputting a voice prompting information which corresponds to the color of the cover of the test tube to be inserted that is determined by the controller: and an image prompting apparatus used for outputting a character prompting information or an image prompting information which corresponds to the color of the cover of the test tube to be inserted that is determined by the controller.

Further, the automatic labeling machine may further include: a casing that has the tube insertion port provided in a surface thereof; a printing apparatus connected to the controller for outputting the identification label; and a labeling apparatus connected to the controller and opposed to the tube insertion port, the labeling apparatus is used for adhering the identification label that is printed out by the printing apparatus to the surface of the inserted test tube.

Further, the printing apparatus may include: a feed roller used for supporting a label paper roll, where a label paper of the label paper roll may include a lining paper and a plurality of labels having fixed length adhered on the lining paper in sequence; a printing mechanism disposed at downstream of the feed roller in a transportation direction of the label paper and used for performing printing on the surface of the label, the printing mechanism includes a print head and a print rubber roller that cooperate tangently with each other; a peeling member disposed at downstream of the printing mechanism in a transportation direction of the label paper and used for peeling the label from the lining paper; a recovery roller located at downstream of the peeling member and used for recovering the lining paper; and a driving mechanism used for driving the print rubber roller and the recovery roller to rotate.

Further, the labeling apparatus may include: a first motor: a drive roller that is drivingly connected to the first motor; and a driven roller, wherein a tube accommodation space is defined between the drive roller and the driven roller and corresponds with the tube insertion port, and the driven roller functions to press the test tube inserted into the tube accommodation space against the drive roller such that the inserted test tube may be caused to rotate about its axis as the first motor drives the drive roller.

Further, the prompting apparatus may include a color prompting apparatus used for outputting a color which corresponds to the color of the cover of the test tube to be inserted that is determined by the controller: where the color prompting apparatus is disposed on the surface of the casing and located at the tube insertion port.

Further, the color prompting apparatus may be formed of a three-primary-color LED, where the controller is used for controlling the three-primary-color LED to pass through setting current such that the color prompting apparatus presents the color of the cover of the test tube to be inserted.

Further, the prompting apparatus may include an image prompting apparatus used for outputting a character or an image prompting information corresponding to the color of the cover of the test tube to be inserted that is determined by the controller, where the image prompting apparatus is positioned on the surface of the casing and disposed to face an operator, and where the controller is used for controlling the image prompting apparatus to display a character or an image corresponding to the color of the cover of the test tube to be inserted.

To achieve above object, in accordance with another aspect of the present disclosure, an automatic labeling machine control method is provided. The automatic labeling machine control method includes: the automatic labeling machine determining the type of a test tube to be inserted; and the automatic labeling machine outputting a prompting information corresponding to the type of the test tube to be inserted.

Further, the automatic labeling machine determining the type of a test tube to be inserted includes the controller of the automatic labeling machine determining a color of a cover of the test tube to be inserted, and the automatic labeling machine outputting a prompting information corresponding to the type of the test tube to be inserted includes a prompting apparatus of the automatic labeling machine outputting the prompting information corresponding to the color of the cover of the test tube to be inserted.

After determining the type of the test tube to be inserted, the automatic labeling machine of the present disclosure may output the prompting information corresponding to the type of the test tube to be inserted, thereby solving the problem of selection error of test tube that is easily caused by the automatic labeling machine in the existing technology.

BRIEF DESCRIPTION OF THE DRAWINGS

The present disclosure will be further understood by the accompanying drawings that constitute a part of the application, and the exemplary embodiments of the disclosure and the following description serve to explain the present disclosure rather than limiting the present disclosure. In the drawings.

DETAILED DESCRIPTION OF THE EMBODIMENTS

It should be appreciated that the embodiments of the present disclosure and features therein could be combined with each other without contradiction. The present disclosure will be described in detail hereinafter with reference to the accompanying drawings and in connection with the embodiments.

Figure 1:
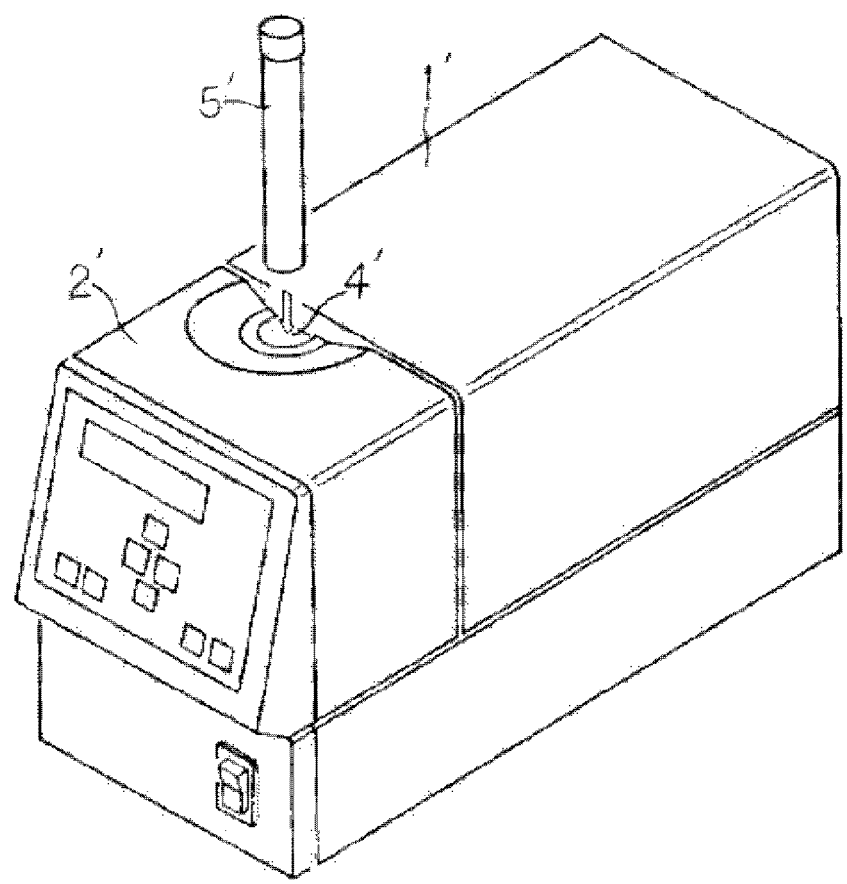
FIG. 1 is a structural view of an automatic labeling machine in existing technology.
Figure 2:
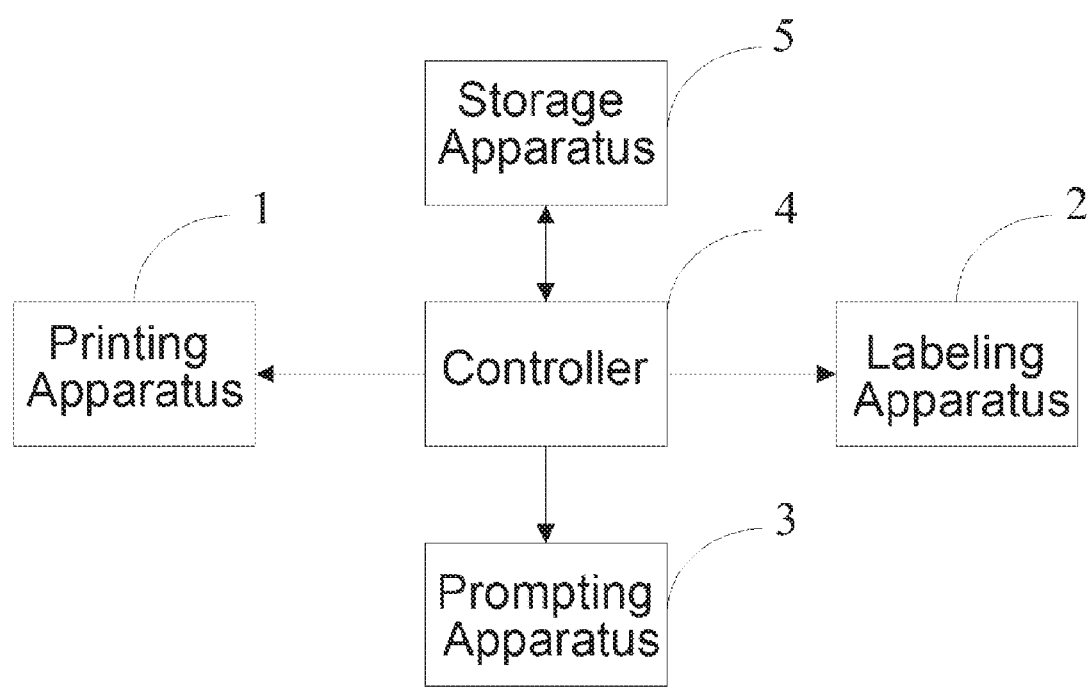
FIG. 2 is a module schematic of an embodiment of an automatic labeling machine according to the present disclosure.

FIG. 2 is a module schematic of an automatic labeling machine according to an embodiment of the present disclosure. The automatic labeling machine can be used for adhering an identification label to a surface of a test tube. As shown in FIG. 2, the automatic labeling machine can include a printing apparatus 1, a labeling apparatus 2, a prompting apparatus 3, a controller 4 and a storage apparatus 5.

The printing apparatus 1, the labeling apparatus 2, the prompting apparatus 3 and the storage apparatus 5 can be electrically connected to the controller 4 that functions to control the operation of various apparatuses. The printing apparatus 1 may be used for printing an identification label including contents such as sample detection information, collector personal information and the like. The labeling apparatus 2 may be employed to adhere the identification label, that is printed by the printing apparatus 1, to the surface of the test tube, and the prompting apparatus 3 may be used for outputting prompting information about the type of the test tube so as to prompt different types of the test tube by outputting different prompting information. For example, the prompting apparatus 3 may output the prompting information on color of a cover of the test tube so as to prompt different color of cover of the test tube by outputting the different prompting information. The prompting apparatus 3 may be one of a color prompting apparatus, a voice prompting apparatus and an image prompting apparatus, or any combinations thereof. In particular, when the prompting apparatus 3 is the color prompting apparatus, the color prompting apparatus is formed by a three-primary-color LED, and the controller 4 can control the three-primary-color LED to pass through the setting current according to the color of the cover of the determined test tube, such that the color prompting apparatus can present a color in consistent with the predetermined color of the cover of the test tube. When the prompting apparatus 3 is the voice prompting apparatus, the controller 4 control the prompting apparatus to output a voice prompting information such as "the user inserts the test tube of  color please" for example, or the like, according to the determined color of the cover of the test tube. Further, when the prompting apparatus 3 is the image prompting apparatus, the image prompting apparatus is formed from electronic elements such as colorful liquid crystals or the like, the controller 4 control the image prompting apparatus to display either character prompting information such as "the user inserts the test tube of  color please" for example, or the like, according to the determined color of the cover of the test tube, or directly display an image of the test tube having a corresponding color cover. The prompting information output by the promping apparatus 3 may be one of character, image, color or voice, or any combinations thereof. The storage apparatus 5 may be a non-volatile memory for storing a correspondence reaction between the type of the test tube and the color of cover of the test tube. The common correspondence reaction between the type of the test tube and the color of cover of the test tube is given in Table 1 below.

| Type of test tube | Color of cover of test tube |
|---|---|
| Tube for general serum | Red |
| Tube for rapid serum | Orange |
| Tube for inertial separation gel coagulant | Auratus |
| Tube for heparinanticoagulant | Green |
| Tube for separation of plasma | Light green |
| Tube for EDTA anticoagulant | Purple |
| Test tube for sodium citrateblood coagulation | Light blue |
| Test tube forsodium citrate blood sedimentation | Black |
| Test tube for potassium oxalate/sodium fluoride | Gray |

In accordance with the automatic labeling machine provided by the present disclosure, the automatic labeling machine may output the prompting information corresponding to the type of the test tube to be inserted after determining the type of the test tube to be inserted, thereby being capable of preventing the problem of the wrong selection of test tube in existing technology from occurring.

The embodiments of the present disclosure further provides an automatic labeling machine control method. The automatic labeling machine control method according to the embodiments of the present disclosure may be a control method for the automatic labeling machine provided by the embodiments of the present disclosure, the automatic labeling machine control method according to embodiments of the present disclosure also may be applied to the automatic labeling machine control method provided by the embodiments of the present disclosure.

Figure 3A:
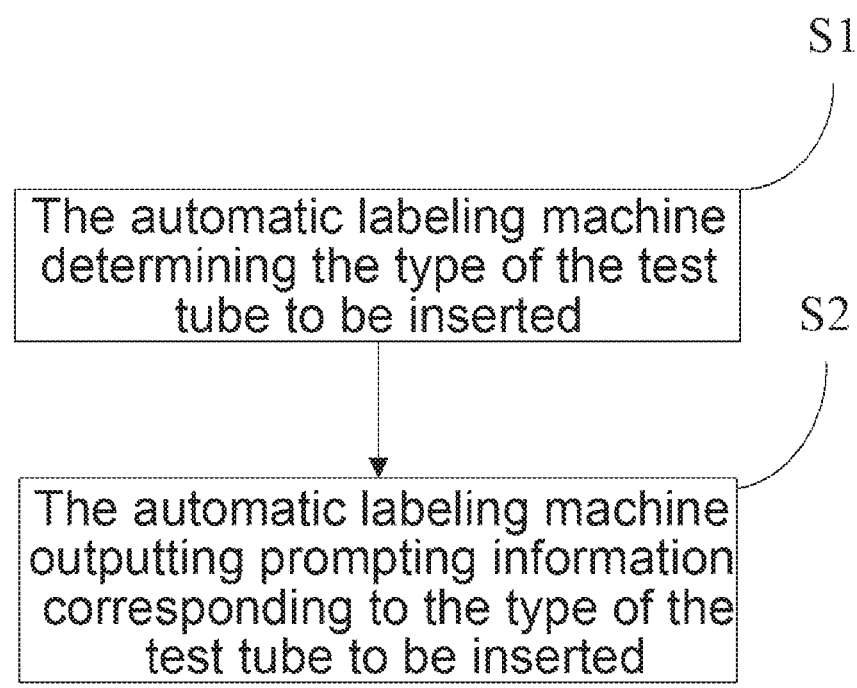
FIG. 3a is a flow chart of an automatic labeling machine control method according to an embodiment of the present disclosure.

FIG. 3a is a flow chart for illustrating the control method of the automatic labeling machine according to an embodiment of the present disclosure.

Step S1: the automatic labeling machine determining the type of test tube to be inserted.

First, the automatic labeling machine receives printing data to be printed on the surface of the label from a host computer, the printing data includes information such as item of detection, date of detection and the name of detected subject, and then the automatic labeling machine determines the type of the test tube according to information on item of detection in the received printing data.

Step S2: the automatic labeling machine outputting the prompting information corresponding to the type of the test tube to be inserted.

After determining the type of the test tube to be inserted, the automatic labeling machine outputs the corresponding prompting information according to the type of the test tube to be inserted. The operator selects the test tube of corresponding type according to the prompting information, and then inserts the test tube into the automatic labeling machine.

Figure 3B:
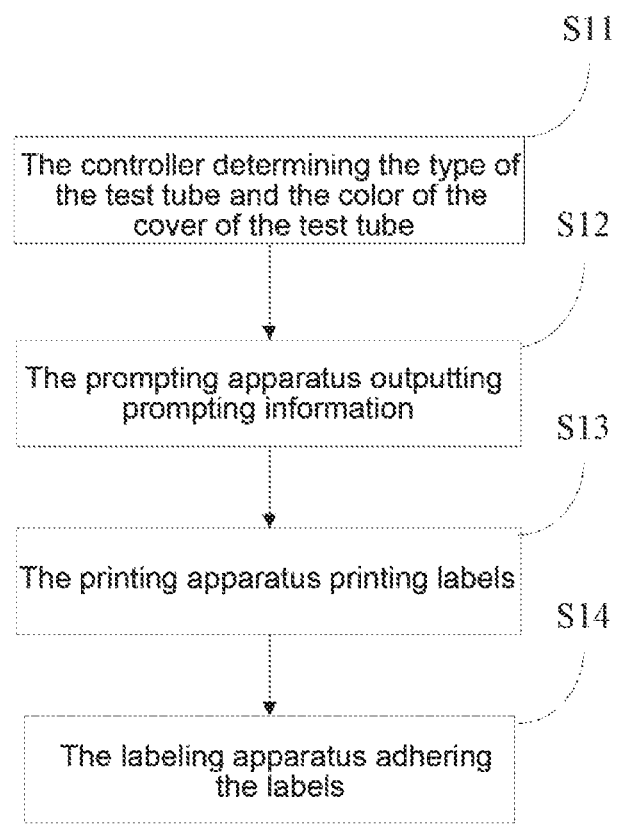
FIG. 3b is a flow chart of the automatic labeling machine control method according to a preferred embodiment of the present disclosure.

FIG. 3b is a flow chart for illustrating an automatic labeling machine control method according to a preferred embodiment of the present disclosure. The automatic labeling machine control method according to this embodiment may be a preferred embodiment of the automatic labeling machine control method according to an embodiment as shown in FIG. 3a. As shown in FIG. 3b, the method includes:

Step S11: the controller determining the type of the test tube and the color of cover thereof.

The controller 4 of the automatic labeling machine receives the printing data, which includes the information such as item of detection, date of detection and the name of detected subject and the like, to be printed on the surface of the label from a host computer, and then determines the type of the test tube according to the information on item of detection in the received printing data. Thereafter, the controller 4 looks up for the correspondence relation between the type of the test tube and the color of the cover of the test tube, that is stored in the storage apparatus 5, thereby determining the color of cover of the test tube to be inserted.

Step S12: the prompting apparatus outputting the prompting information.

The controller 4 controls the prompting apparatus 3 to output the corresponding prompting information according to the color of the cover of the test tube to be inserted. Thus, the operator can select the test tube with the cover of the corresponding color according to the prompting information, and then insert the test tube into the labeling apparatus 2.

Step S13: the printing apparatus printing labels.

The controller 4 controls the printing apparatus 1 to print the printing data on the surface of the label and output the printed label from its discharge port to the labeling apparatus 2.

Step S14: the labeling apparatus adhering the labels.

The controller 4 controls the labeling apparatus 2 to adhere the label output by the printing apparatus 1 to the surface of the test tube.

In accordance with the automatic labeling machine of the present disclosure, the controller can determine the type of the test tube and the color of the cover thereof according to the printed data before the test tube is inserted at each time, and can control the prompting apparatus to output one or more prompting information in the form of color, character, image or voice. The operator can select the test tube with the corresponding color cover according to the prompting information, which has a better visualization and reliability, and thus the problem of the wrong detection result caused by wrong selection of test tube can be avoided.

Figure 4:
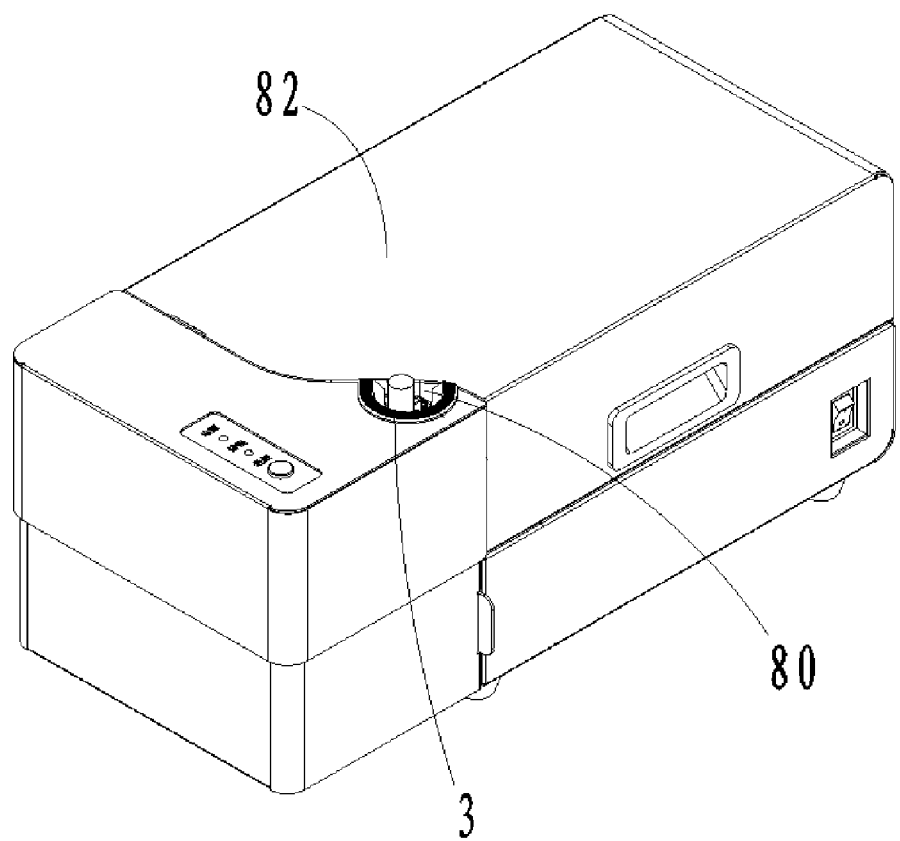
FIG. 4 is an external view of the automatic labeling machine according to an embodiment of the present disclosure.
Figure 5:
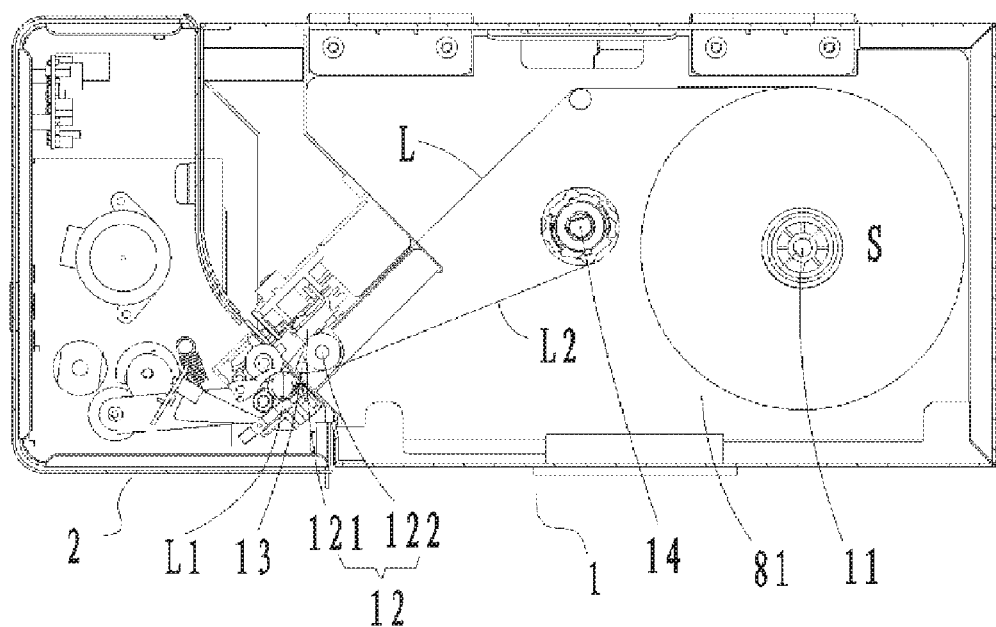
FIG. 5 is a structural view of an internal structure of the automatic labeling machine according to an embodiment of the present disclosure.

FIG. 4 is an external schematic view of the automatic labeling machine according to an embodiment of the present disclosure, and FIG. 5 is a schematic view of an inner structure of the automatic labeling machine according to an embodiment of the present disclosure. As illustrated in FIGS. 4-5, a casing of the automatic labeling machine includes a bottom plate 81 and a top shell 82. The top shell 82 and the bottom plate 81 together define the accommodating space for the printing apparatus 1 and the labeling apparatus 2. The surface of the top shell 82 has a tube insertion port 80 provided therein through which the test tube is inserted, and both the printing apparatus 1 and the labeling apparatus 2 are supported by the bottom plate 81. The labeling apparatus 2 is positioned at a discharge port of the printing apparatus 1 and is opposite to the tube insertion port 80. The test tube may be inserted into the labeling apparatus 2 through the tube insertion port 80. Thus, the label that is printed by and output from the printing apparatus 1 can be adhered to the surface of the test tube by the labeling apparatus 2.

The printing apparatus 1 includes a feed roller 11, a printing mechanism 12, a peeling member 13 and a recovery roller 14. The feed roller 11 is used for supporting a label paper roll S. A label paper L is made up of a lining paper L2 and a plurality of labels L1 having a fixed length that are adhered on the lining paper L2 in sequence. The printing mechanism 12 is located at downstream of the feed roller 11 in a direction of transportation of the label paper L, and used for printing set contents, such as collector information, detection information and the like, on the surface of the label L1. The printing mechanism 12 includes a print head 121 and a print rubber roller 122 that cooperate tangently with each other. An axis of the print rubber roller 122 is parallel to an axis of the feed roller 11. The print rubber roller 122 is drivingly connected to a driving mechanism of the printing apparatus, and can rotate around its axis when being driven by the driving mechanism. The label paper L passes between the print head 121 and the print rubber roller 122, where a print face of the label L1 contacts with the print head 121 and the lining paper L2 contacts with the print rubber roller 122, the print rubber roller 122 can drive the label paper L to be transported toward downstream of the printing mechanism 12 when it is driven to rotate by the driving mechanism. The peeling member 13 is disposed at downstream of the printing mechanism 12 in a transportation direction of the label paper L and used for peeling the label L from the lining paper L2. When the label paper L is being output by the printing mechanism 12, the lining paper L2 of the label paper L contacts with the peeling member 13, passes through the peeling member 13 and continues to be transported downstream of the peeling member 13. In the embodiment, the peeling member is in the form of shaft-shaped. In other embodiments, the peeling member may be in the form of plate-shaped. Further, the recovery roller 14 is located at downstream of the peeling member 13 in a transportion direction of the lining paper L2 and used for recovering the lining paper L2 of the label paper L. The recovery roller 14 is drivingly connected to the driving mechanism of the printing apparatus 1 and is able to rotate around its axis thereof when being driven by the driving mechanism.

While the printing apparatus 1 is printing, the label paper L is lead out from the label paper roll S on the feed roller 1, and passes between the print head 121 and the print rubber roller 122. A tip of the lining paper L2 of the label paper L is wound around the recovery roller 14 after bypassing the peeling member 13. The driving mechanism of the printing apparatus 1 drives the print rubber roller 122 and recovery roller 14 to rotate. The print rubber roller 122 transports the label paper L towards downstread, and at the same time, the print head 121 performs printing on the surface of the label L1, and the take-up roller 14 rewinds the lining paper L2, the label L1 is separated from the lining paper L2 at the peeling member 13. As a result, the label L1 is output from the discharge port of the printing apparatus 1 toward the labeling apparatus 2 as driven by the print rubber roller 122.

Figure 6:
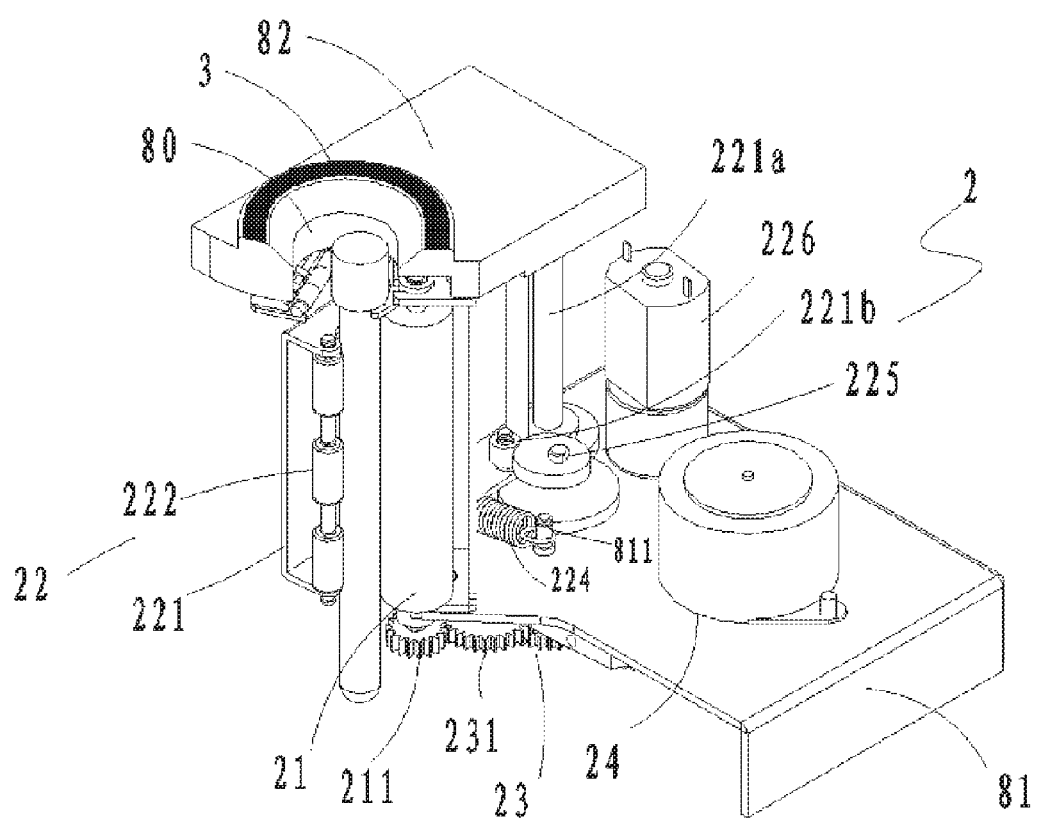
FIG. 6 is a structural view of a labeling apparatus of the automatic labeling machine according to an embodiment of the present disclosure.
Figure 7:
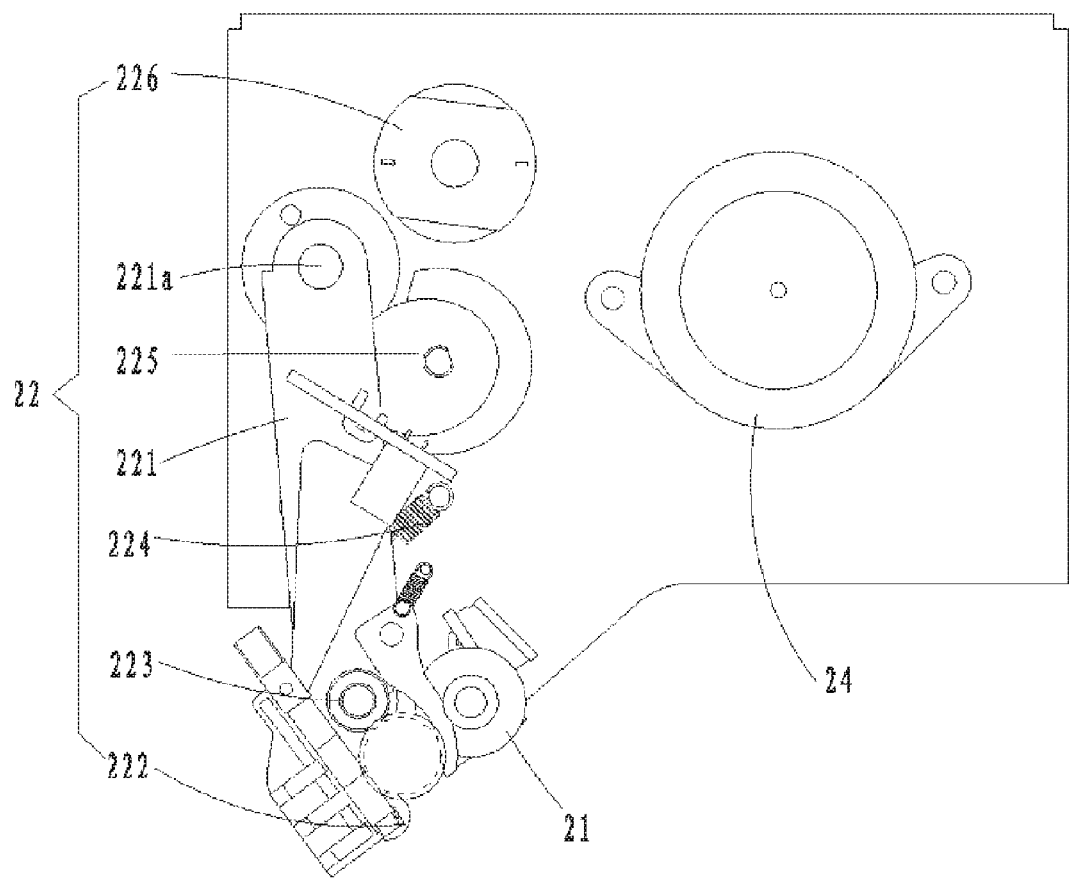
FIG. 7 is a structural top view of a labeling apparatus of the automatic labeling machine according to an embodiment of the present disclosure.

The labeling apparatus 2 is located at the discharge port of the printing apparatus 1 and used for adhering the label L1 output by the printing apparatus to the surface of the test tube FIG. 6 is a schematic structure view of the labeling apparatus of the automatic labeling machine according to an embodiment of the present disclosure. FIG. 7 is a structural top view of the labeling apparatus of the automatic labeling machine according to an of the present disclosure. As shown in FIGS. 6 and 7, the labeling apparatus 2 is disposed on the bottom plate 81, and includes a drive roller 21, a driven roller assembly 22, a transmission assembly 23 and a first motor 24.

The drive roller 21 is supported by the bottom plate 81 and can freely rotate around an axis itself. The drive roller 21 is provided with a gear 211 at its shaft end so as to drivingly connect with the transmission assembly 23. The first motor 24 is fixedly mounted on the bottom plate 81 and can drive the drive roller 21 to rotate by the transmission assembly 23. The transmission assembly 23 is located between the first motor 24 and the gear 211 at the shaft end of the drive roller 21 and used for transmitting the torque output by the first motor 24 to the drive roller 21. The transmission assembly 23 may include parts such as a toothed belt, a gear, etc. In this embodiment, the transmission assembly 23 includes a gear set, and one gear (not shown) in the gear set is meshingly connected to a motor gear (not shown in the drawings) that is fixed on an output shaft of the first motor 24, while the other gear 231 in this gear set is meshingly connected to the gear 211 at the shaft end of the drive roller 21. As the output shaft of the first motor 24 rotates, the drive roller 21 may be driven to rotate by the transmission assembly 23.

The driven roller assembly 22 can press the test tube against the driver roller 21, thus when the drive roller 21 rotates, the test tube may be driven to rotate around an axis itself. The driven roller assembly 22 may include a bracket 221, a first driven roller 222, a second driven roller 223, an elastic member 224 and a driving assembly. A tube accommodation space is defined among the drive roller, the first driven roller 222 and the second driven roller 223 and correspond to the tube insertion port 80. After being inserted through the tube insertion port 80, the test tube enters the tube accommodation space. The first driven roller 222 and the second driven roller 223 function to press the test tube inserted into the tube accommodation space against the drive roller 21, such that the inserted test tube can be brought to rotates around its axis when the first motor 24 drives the drive roller 21 to rotate. One end of the bracket 221 is connected to the bottom plate 81 through a support shaft 221*a*, and the bracket 221 can swing about the support shaft 221*a*. In particular, the support shaft 221*a* is vertically supported on the bottom plate 81 and is fixed connected to the bottom plate 81. The first driven roller 222 and the second driven roller 223 are disposed on the bracket 221 in a spaced-apart way. When the bracket 221 swings about the support shaft 221*a*, the first driven roller 222 and the second driven roller 223 rotate around the support shaft 221*a* together. Both an axis of the first driven roller 222 and an axis of the second driven roller 223 are parallel to that of the drive roller 21, and can freely rotate around the respective axis: and furthermore, distance therebetween is smaller than an outer diameter of the test tube having a minimum outer diameter supported by the automatic labeling machine. An end of the elastic member 224 is connected to the bracket 221, while the other end thereof is connected to a hook post 811 on the bottom plate 81. There is always a motion trend that the bracket 221 always swings about the support shaft 221*a* along a first direction so that the first driven roller 222 and the second driven roller 223 on the bracket 221 are pressed toward the drive roller 21, under the function of the elastic force of the elastic member 224.

The driving assembly may be used for driving the bracket 221 to swing in a direction opposite to the first direction, which allows the first driven roller 222 and the second driven roller 223 located on the bracket 221 to move in a direction away from the drive roller 21. As the first driven roller 222 and the second driven roller 223 move away from the drive roller 21 a set distance, the test tube can be inserted through the tube insertion port 80 and thus be positioned among the drive roller 21, the first driven roller 222 and the second driven roller 223.

According to the present embodiment, the driving assembly may include a cam 225 pivotally connected to the bottom plate 81 and a second motor 226 drivingly connected to the cam 225. Further, the cam 225 is disposed on one side of the bracket 221 adjacent the drive roller 21, and can rotate around its pivot thereof by the driving of the second motor 226, so as to abut against or disengage from the bracket 221. When the cam 225 has rotated a set angle around its pivot thereof along a set direction, the cam 225 abuts against the bracket 221 and then drives the bracket 221 to over come the elastic force of the elastic member 224 so as to rotate about the support shaft 221a to a set position in a direction away from the drive roller 21. At this moment, the first driven roller 222 and the second driven roller 223 is spaced apart from the drive roller 21 a set distance. In this embodiment, the cam 225 contacts with a rolling wheel 221b on the bracket 221, thereby reducing the friction between the cam 225 and the bracket 221. When the cam 225 rotates around its pivot thereof in an opposite direction to the set direction to a position separated from the bracket 221, the bracket 221 rotates around the support shaft 221a in a direction closing the drive roller 21 under the function of the elastic force of the elastic member 224, and in this way, the first driven roller 222 and the second driven roller 223 press the test tube against the drive roller 21. At this point, the test tube may be driven to rotate around its axis itself if the drive roller 21 rotates.

According to this embodiment, the prompting apparatus 3 may be a color prompting apparatus that is disposed on the surface of the top shell 81. Preferably, the color prompting apparatus is placed at the tube insertion port 80 and surrounds the tube insertion port 80. The color prompting apparatus is formed of a three-primary-color LED. When the controller controls the three-primary-color LED to pass through the setting current, the color prompting apparatus may present the predefined color of the cover of the test tube. In this embodiment, the operator can insert the test tube with cover color being consistent with the color of the color promping apparatus according to the color indicated by the color promping apparatus to facilitate judgement of operation by the operator, because the color promping apparatus is disposed at the tube insertion port 80. In addition, once the color of the cover of the inserted test tube is inconsistent with the color surrounding the tube insertion port 80, the operator can find out it immediately by distinct color contrast and thus make a correction. Therefore, the wrong selection of test tube can be avoided.

Figure 8:
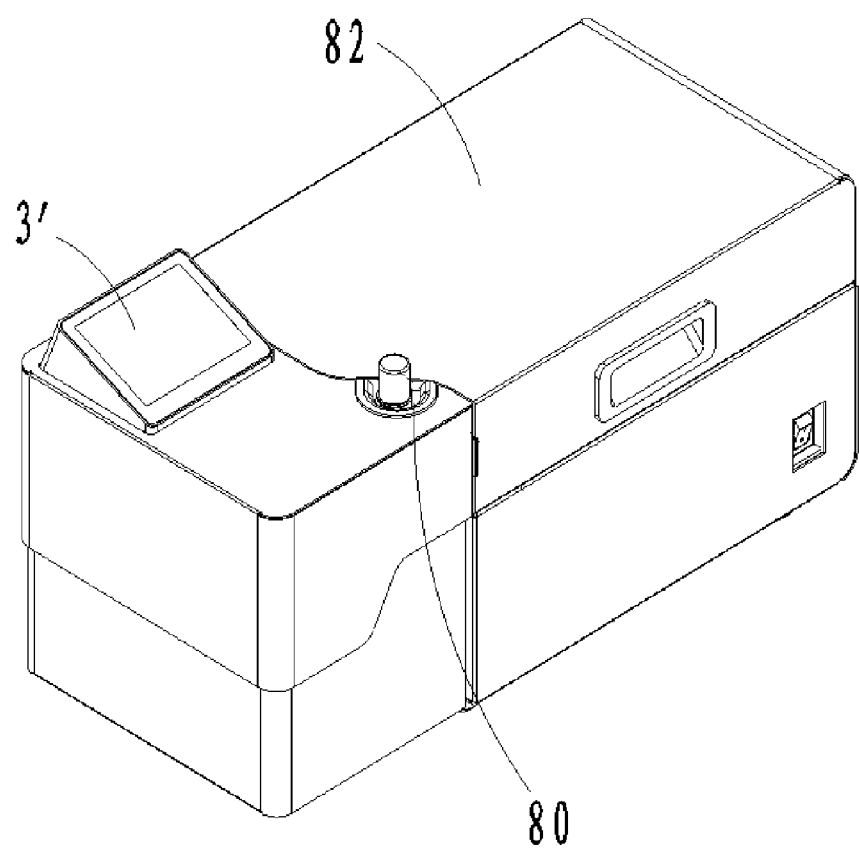
FIG. 8 is a an external schematic view of the automatic labeling machine according to an another embodiment of the present disclosure.

FIG. 8 is an external view of the automatic labeling machine according to another embodiment of the present disclosure. As shown in FIG. 8, the prompting apparatus in this embodiment is an image prompting apparatus 3' that is made up of electronic elements such as colorful liquid crystal or the like. The image prompting apparatus 3' is located on the surface of the top shell 82 and is adjacent to the tube insertion port 80 and is incliningly diposed toward the operator. After determining the color of the cover of the test tube, the controller 4 controls the image prompting apparatus 3' to display character prompting information such as "please inserting the test tube of ** color, or directly display an image of the test tube having the cover of the corresponding color. The operator can select a test tube in accordance with the character or image displayed on the image prompting apparatus 3'. Because the image prompting apparatus 3' is disposed to face the operator, such prompting information may always appear in the view filed of the operator when the operator inserts the test tube, thereby reminding the operator at all times and avoiding the problem on the wrong selection of the test tube.

The foregoing description of the preferred embodiment of the present disclosure is merely illustrative, rather than limiting the scope of the present disclosure. Those skilled in the art will appreciate that a variety of apparent alterations and changes can be made without departing from the protection scope of the disclosure. Any modifications, equivalent replacements and improvements made within the spirit and principle of the disclosure shall be included in the protection scope of the disclosure.

The invention claimed is:

1. An automatic labeling machine for adhering an identification label to a surface of a test tube, comprising:
   a tube insertion port (80) for inserting the test tube;
   a controller (4) for determining a type of the test tube to be inserted;
   a prompting apparatus (3) connected to the controller (4) and used for outputting prompting information corresponding to the type of the test tube to be inserted; and
   a storage apparatus (5) for storing a correspondence relation between the type of the test tube and the color of the cover of the test tube,
   wherein the controller (4) is used for determining a color of a cover of the test tube to be inserted;
   the prompting apparatus(3) is used for outputting the prompting information corresponding to the color of the cover of the test tube to be inserted;
   the controller (4) is connected to the storage apparatus (5), so as to receive printed data which is to be printed on the surface of the label to be adhered on the surface of the test tube, determine the type of the test tube to be inserted according to the printed data, and then search for the correspondence relation between the type of the test tube and the color of the cover of the test tube stored in the storage apparatus (5) and determine the color of the cover of the test tube to be inserted according to the type of the test tube to be inserted.

2. The automatic labeling machine of claim 1, wherein the prompting apparatus (3) comprise at least one of the following prompting apparatuses:
   a color prompting apparatus used for outputting a color which corresponds to the color of the cover of the test tube to be inserted that is determined by the controller (4);
   a voice prompting apparatus used for outputting voice prompting information which corresponds to the color of the cover of the test tube to be inserted that is determined by the controller (4); and
   an image prompting apparatus used for outputting a character prompting information or an image prompting information which corresponds to the color of the cover of the test tube to be inserted that is determined by the controller (4).

3. The automatic labeling machine of claim 1, further comprising:
   a casing that has the tube insertion port (80) provided in a surface of the casing;

a printing apparatus (1) connected to the controller (4) for outputting the identification label; and a labeling apparatus (2) connected to the controller (4) and opposed to the tube insertion port (80), the labeling apparatus (2) is used for adhering the identification label that is printed out by the printing apparatus (1) to the surface of the inserted test tube.

4. The automatic labeling machine of claim 3, wherein the prompting apparatus (3) comprises:

a color prompting apparatus used for outputting a color which corresponds to the color of the cover of the test tube to be inserted that is determined by the controller (4);

wherein the color prompting apparatus is disposed on the surface of the casing and located at the tube insertion port (80).

5. The automatic labeling machine of claim 4, wherein the color prompting apparatus is formed of a three-primary-color Light-Emitting Diode (LED), and the controller (4) is used for controlling the three-primary-color LED to pass through setting current such that the color prompting apparatus presents the color of the cover of the test tube to be inserted.

6. The automatic labeling machine of claim 3, wherein the prompting apparatus (3)comprises:

an image prompting apparatus used for outputting a character or image prompting information corresponding to the color of the cover of the test tube to be inserted that is determined by the controller (4), wherein the image prompting apparatus is disposed on the surface of the casing and disposed to face an operator, wherein the controller (4) is used for controlling the image prompting apparatus to display a character or an image corresponding to the color of the cover of the test tube to be inserted.

7. An automatic labeling machine control method for the automatic labeling machine of claim 1, comprising:

determining a type of a test tube to be inserted by an automatic labeling machine; and outputting prompting information corresponding to the type of the test tube to be inserted by the automatic labeling machine.

8. The automatic labeling machine control method of claim 7, wherein determining the type of a test tube to be inserted by the automatic labeling machine, comprises:

determining a color of a cover of the test tube to be inserted by a controller of the automatic labeling machine, and outputting a prompting information corresponding to the type of the test tube to be inserted by the automatic labeling machine comprises:

outputting the prompting information corresponding to the color of the cover of the test tube to be inserted by a prompting apparatus of the automatic labeling machine.

* * * * *